US00PP35629P2

(12) United States Plant Patent
Hansen

(10) Patent No.: US PP35,629 P2
(45) Date of Patent: Jan. 30, 2024

(54) ***SEDUM* PLANT NAMED 'STRAWBERRY MILKSHAKE'**

(50) Latin Name: ***Sedum* hybrid**
Varietal Denomination: Strawberry Milkshake

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/445,007

(22) Filed: Feb. 22, 2023

(51) Int. Cl.
*A01H 5/02* (2018.01)
*A01H 6/32* (2018.01)

(52) U.S. Cl.
USPC ..... Plt./479

(58) Field of Classification Search
USPC ..... Plt./479

CPC ... A01H 5/12; A01H 5/02; A01H 5/00; A01H 6/32; A01H 6/328
See application file for complete search history.

(56) References Cited

PUBLICATIONS

Gilbert H. Wild & Son Issuu retrieved on Jun. 29, 2023 at https://issuu.com/pallensmith/docs/_22_spring_catalog, cover page and p. 2 (Year: 2022).*
Provisional Plant U.S. Appl. No. 63/372,297, filed Mar. 1, 2022, 5 pp. (Year: 2022).*

* cited by examiner

*Primary Examiner* — June Hwu

(57) ABSTRACT

A new and distinct ornamental perennial *Sedum* plant named 'Strawberry Milkshake' is characterized by tight-forming upright mounds of vertical stems with glaucous deep purplish-bronze foliage that resists powdery mildew and subsequent scaring. The numerous, stems are highly branched and resist lodging in the summer heat and rains. Flower buds are purplish-red opening to light-pink completely covering the top of the plant, and developing persistent rosy-purple ovaries. The new plant is useful for the landscape in containers, as specimens or en masse.

1 Drawing Sheet

Botanical designation: *Sedum* hybrid.
Cultivar denomination: 'Strawberry Milkshake'.

STATEMENT REGARDING PRIOR DISCLOSURES UNDER 37 CFR 1.77(B)(6)

No plants of *Sedum* 'Strawberry Milkshake' have been sold or offered for sale in this country or anywhere in the world nor has any disclosure of the new plant been made more than one year prior to the effective filing date of this application, and such sale or disclosure within one year was either derived directly or indirectly from the inventor and would be a 35 U.S.C. 102(b) exception.

BACKGROUND OF THE INVENTION

The present invention relates to a new and distinct cultivar of *Sedum* plant, botanically known as *Sedum* and hereinafter referred to by the cultivar name 'Strawberry Milkshake'.

The new *Sedum* plant is a selection of a planned breeding program conducted by the inventor, at a wholesale perennial nursery in Zeeland, Michigan, USA.

The new *Sedum* plant was selected from self-pollination in an isolation area of a proprietary, unreleased, unnamed hybrid known only by the breeder code 14-61-2 at a wholesale perennial nursery in Zeeland, Michigan on Jun. 1, 2015. The seeds were collected in the fall of 2015. *Sedum* 'Strawberry Milkshake' was assigned the breeder code number 15-17-1 to keep it separated from among thousands of other seedlings of this and other crosses when it progressed through the initial trial phase in the fall of 2017. The selected single seedling clone was originally selected for it strong, healthy, dense growth, colorful foliage and flowers.

Asexual reproduction of *Sedum* 'Strawberry Milkshake' by division at a wholesale perennial nursery in Zeeland, Michigan, USA since October of 2018, and subsequent vegetative shoot tip cuttings has shown that the unique features of this new *Sedum* plant are stable and reproduced true to type in successive generations.

SUMMARY OF THE INVENTION

Plants of *Sedum* 'Strawberry Milkshake' have not been observed under all possible environmental conditions. The phenotype may vary somewhat with variations in environment such as temperature, available water, fertility and light intensity without, however, any variation in genotype.

The following traits have been repeatedly observed and are determined to comprise the unique characteristics of *Sedum* 'Strawberry Milkshake' and distinguish it as a new and distinct autumn stonecrop plant unique from all other autumn stonecrop plants known to the inventor:

1. Tight-forming upright mounds with vertical stems;
2. Center stems remain erect throughout the growing season producing full habit;
3. Glaucous, deep purplish-bronze foliage resists powdery mildew and the subsequent scaring;
4. Numerous stems produce dense flower clusters of light-pink completely cover the mounded plant;

5. Flower buds are purplish-red opening to light pink and develop persistent rosy-purple carpels;

The parent is not as dense basal branching and does not retains its upright stems as well through the entire growing season.

The nearest comparison varieties known to the inventor are: 'Night Embers' U.S. Plant Pat. No. 29,211, 'Xenox' U.S. Plant Pat. No. 16,888, 'Neon' (not patented), 'Black Jack' U.S. Plant Pat. No. 16,736, 'Coraljade' U.S. Plant Pat. No. 33,958, 'Back in Black' U.S. Plant Pat. No. 33,632, and 'Tiarmisu' U.S. Plant Pat. No. 33,781.

'Night Embers' is slightly taller and narrower in habit with darker foliage and darker flowers. 'Xenox' a similar height, but narrower and more open habit and the flowers are less abundant and cover less of the mound. 'Neon' has a similar height, but is more upright and narrower in habit, the foliage is light green, and the flowers are a single tone of rosy-magenta. 'Black Jack' has a narrower habit, the foliage is more greyed-purple, the flowers are deep garnet, and the foliage is more susceptible to powdery mildew infection. 'Coraljade' has lighter gray-green foliage and stems with citron-green flower buds and soft coral-colored flowers. 'Back in Black' has broader and darker leaves, stems that are more upright and narrower habit, the flowers are light pink and carpels become deep garnet. 'Tiramisu' has smaller habit with smaller narrower leaves that are lighter bronze-colored, and the flowers open cream from pink blushed buds on smaller inflorescences with thinner stems and less dense flowering.

BRIEF DESCRIPTION OF THE PHOTOGRAPHS

The photograph of the new plant demonstrates the unique traits and the overall appearance of *Sedum* 'Strawberry Milkshake'. The colors are as accurate as reasonably possible with color reproductions of this type. Variations in ambient light spectrum, source and direction may cause the appearance of minor variation in color. The plants used in the photograph were three-year-old plants grown in an open, full-sun trial garden at a wholesale perennial nursery in Zeeland, Michigan with supplemental water and fertilizer when needed. No plant growth regulators or pinching have been used.

DETAILED BOTANICAL DESCRIPTION

Figure 1:
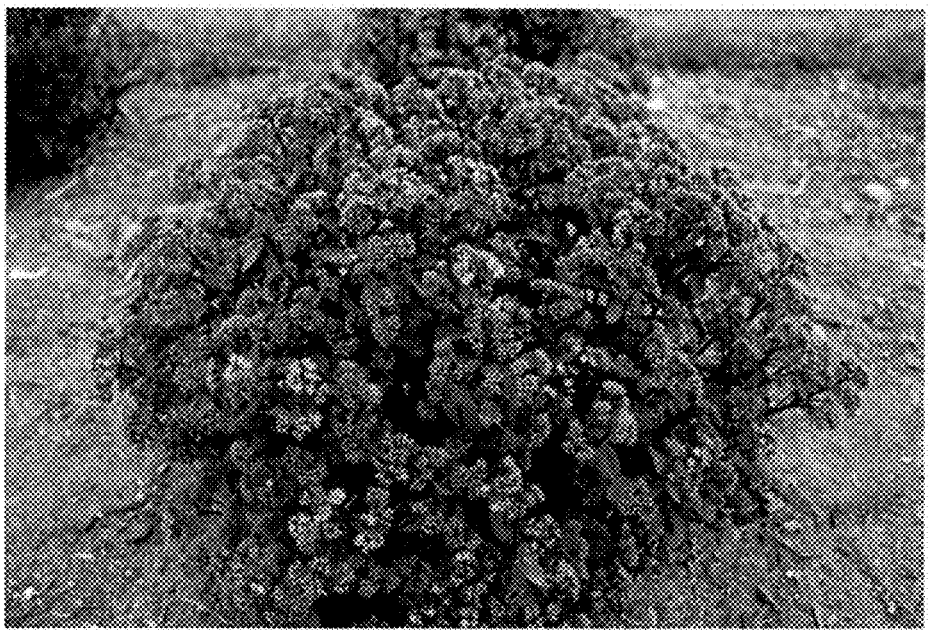
FIG. 1 shows the habit of the new plant with foliage in early stages of flowering.
Figure 2:
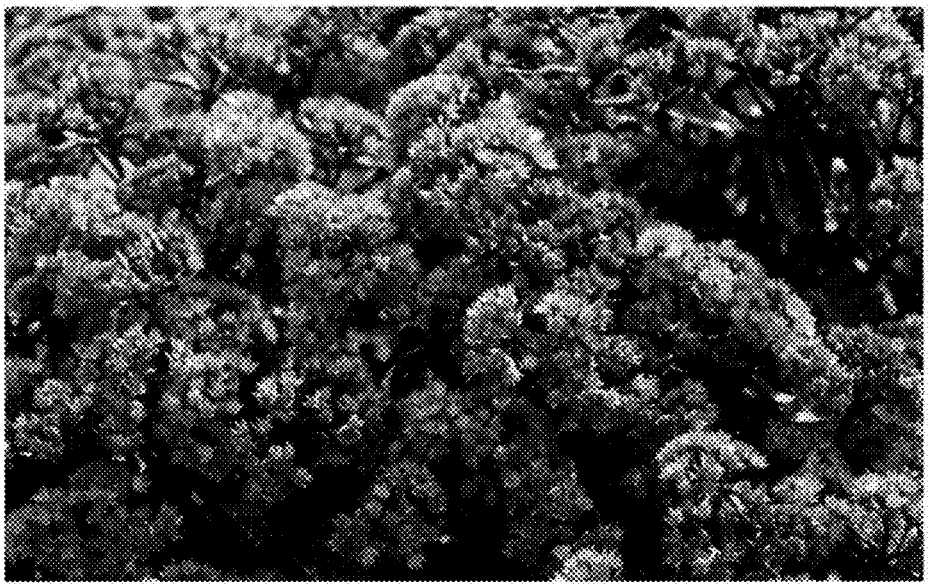
FIG. 2 shows a close-up of the flowers and buds of the new plant in mid-summer.

The following is a detailed description of three-year-old plants of the new cultivar as grown outdoors in a full sun trial plot at a wholesale nursery in Zeeland, Michigan. No plant growth regulators have been used. Plants of the new cultivar have not been tested under all possible conditions. The phenotype may vary with changes in the environment, climate, and cultural conditions without change however in the genotype. The color reference is in accordance with the 2015 edition of The Royal Horticultural Society Colour Chart except where general color dictionary terms are used.

Parentage: Self-pollination of the unreleased, unnamed proprietary hybrid known only by the breeder code 14-61-2;

Asexual propagation: Stem tip cuttings and division;

Time to initiate roots: About two weeks;

Time to finish a 3.8-liter flowering container: About three months in the summer from a rooted 2.5 cm plug;

Root description: Thick, fleshy; freely branching; creamy white to light tan in color;

Plant habit: Winter-hardy herbaceous perennial; upright mound; stiff upright stems; dense and full, not opening in center later in the season; flower heads freely branching;

Growth rate: Moderately vigorous;

Plant size: About 58 cm tall and 87 cm wide in full flower;

Stems: Terete, hollow; glaucous; glabrous; diameter at base to about 11 mm, average about 9 mm; heavily branched in distal portion; about 22 cm long from base to initial branches; to about 55 stems per plant and 10 to 15 branches per stem;

Stem color: Variable; nearest RHS N186D and between a blend of RHS N186D and RHS N187C;

Lateral branches: To about 10 to 15 per stem; glaucous; glabrous; terete, hollow; primary branches to about 30 cm long and about 5.5 mm diameter at base;

Lateral branch color: Nearest RHS 187C;

Foliage: Oval; sub-opposite; flat to slightly calathiform; simple; smooth; sarcous; glabrous and dull on both surfaces; sessile; thick; apex bluntly acute; base rounded; margin irregularly and shallowly dentate, 5 to 12 teeth per leaf side, on distal portion; teeth average about 5.0 mm apart; attitude outward; about 15 leaves per stem below branches;

Foliage size: To about 8.8 cm long, 5.2 cm across and 2 mm thick; average about 6.2 cm long, 3.8 cm across and 2 mm thick; decreasing distally;

Foliage color: Adaxial young nearest RHS 137B lightly maculate with nearest RHS N186C, abaxial young between RHS 148B and RHS 148C lightly maculate with nearest RHS N186C; mature adaxial nearest RHS N186B with an undertone of nearest RHS 191A, mature abaxial nearest RHS 148B moderately maculate with nearest RHS N186C;

Petiole: Leaves sessile;

Venation: Palmate, indistinguishable; abaxial midrib slightly raised;

Vein color: Adaxial proximal midrib nearest RHS N186C and distally indistinguishable from surrounding leaf, abaxial midrib nearest RHS N186C; secondary veins both adaxial and abaxial not obvious;

Flower: Stellate; actinomorphic; pentamerous; persistent; attitude upright to outwardly in terminal compound cymes; size to about 6 mm across and 5 mm deep;

Flower number: To about 60 to 210 per branch and 800 to 1,200 flowers per stem and 8,000 to 14,000 per plant;

Fragrance: None detected;

Flowering season: Beginning late August in Zeeland, Michigan for about three weeks;

Longevity: Flower cymes remain effective for about three weeks on the plant and one week as cut flowers; individual flowers and calyces persistent and effective for about three weeks;

Flower buds about one day prior to opening: Ellipsoidal; apex acute; base truncate; about 4.5 mm long and about 2.5 mm diameter near middle;

Flower bud color: Distally nearest RHS 59A transitioning just above calyx to between RHS 62D and RHS NN155D; calyx nearest RHS 176C proximally with apices nearest RHS 187C;

Inflorescence: To about 20 cm tall from first branch and about 16 cm across;

Petals: Typically five; lanceolate; acute apex; base truncate and fused; margin entire; glabrous abaxial and adaxial; average about 5 mm long and about 2 mm across near middle;

Petal color: Young adaxial nearest RHS 64A in distal one-half lightening proximally to nearest RHS NN155D with slight blush of nearest RHS 64A; young abaxial distal one-half nearest RHS 60B and proximally lightening to nearest RHS NN155D with light blush of nearest RHS 60B; mature adaxial distally nearest RHS 60B and proximally nearest RHS NN155D with light blush nearest RHS 60B; abaxial distal one-third nearest RHS 60A and proximally between RHS 62D and RHS NN155D with light blush of nearest RHS 60B;

Calyx: With five sepals; campanulate to stellate; about 2.5 mm across and 2 mm deep;

Sepals: Linear to lanceolate; narrowly acute apex; fused in basal 1 mm; entire margin; glabrous and slightly glaucous both abaxial and adaxial; adpressed to petals, about 2 mm long and about 1 mm across at fusion;

Sepal color: Abaxial and adaxial nearest RHS 59A;

Peduncles: Terete, hollow; glaucous, glabrous; stiff and flexible; freely branching; mostly upwardly to slightly outwardly; with branches to about 45° from perpendicular; about 5 cm long and 3 mm diameter;

Peduncle color: Between RHS 187B and RHS 187C;

Pedicels: Cylindrical; glabrous; glaucous; strong and stiff, yet flexible; to about 4 mm long and 0.6 mm diameter; average about 3 mm long and 0 mm diameter;

Pedicel color: Nearest RHS 182B;

Androecium: Ten;

*Filaments*.—Ten, five adnate the lower 1.5 mm of adaxial petals and five attached between petals at the base of the ovaries; cylindrical; glabrous; filaments attached to base of ovary to about 4 mm long and about 0.3 mm diameter, filaments adnate to petals about 3.5 mm long and 0.3 mm diameter; color initially nearest RHS NN155D maturing to between RHS 62D and RHS NN155D with a blush of nearest RHS 62A.

*Anther*.—Ten; ellipsoidal; basifixed; longitudinal; about 0.7 mm long and 0.5 mm across; color between RHS 42A and RHS 42B.

*Pollen*.—Abundant; less than 0.1 mm across; color nearest RHS 18B.

Gynoecium: Typically five; cylindrical, conic in distal one-third; about 3.5 mm long and 1.2 mm diameter;

*Style*.—Terete; tapering distally and base truncate; about 0.5 mm long and 0.2 mm diameter at point of attachment to ovary; glabrous; lustrous; color nearest RHS 64D to strongly blushed with RHS 64B.

*Stigma*.—Minute, acute; about 0.2 mm diameter and 0.1 mm long; color nearest RHS 64B.

*Ovary*.—Nearly terete; acutely tapering at apex to style; base truncate; lustrous; persistent; about 3 mm long and 1.2 mm diameter; color nearest RHS N155D with faint blush of nearest RHS 64B, developing with maturity to distally nearest RHS 59A and proximally nearest RHS 160D.

Fruit and seed have not been observed.

Growing conditions: Plants of the new *Sedum* 'Strawberry Milkshake' are xeromorphic and grow best with good drainage, full sun and moderate to low fertility. The new plant is cold hardy from USDA zones 3 to 9 and has tolerated temperatures of at least 35 degrees C. 'Strawberry Milkshake' tolerates heavy rains and wind and is not prone to develop an open center later in the season as many other *Sedum* cultivars do that are known to the inventor.

Disease and pest resistance: Other pest and disease resistance and tolerance outside that normal for *Sedum* is not known.

It is claimed:

1. A new and distinct perennial *Sedum* plant named 'Strawberry Milkshake' as herein described and illustrated.

* * * * *